(12) United States Patent
O'Neil

(10) Patent No.: US 6,951,833 B2
(45) Date of Patent: Oct. 4, 2005

(54) ANTI-MICROBIAL COMPOSITIONS

(76) Inventor: Deborah O'Neil, 7143 Keystone St., Studio 240, Philadelphia, PA (US) 19135

(*) Notice: Subject to any disclaimer, the term of this patent is extended or adjusted under 35 U.S.C. 154(b) by 0 days.

(21) Appl. No.: 10/663,101

(22) Filed: Sep. 16, 2003

(65) Prior Publication Data

US 2004/0127385 A1 Jul. 1, 2004

Related U.S. Application Data

(60) Provisional application No. 60/411,329, filed on Sep. 17, 2002.

(51) Int. Cl.$^7$ ................................................ A61K 7/00

(52) U.S. Cl. ........................ 510/130; 510/131; 510/156; 510/481; 510/438; 424/74; 424/401; 424/405; 424/724; 424/764

(58) Field of Search ................................. 510/131, 438, 510/130, 156, 424; 424/74, 764, 724, 401, 405

(56) References Cited

U.S. PATENT DOCUMENTS

| | | | |
|---|---|---|---|
| 3,203,863 A | | 8/1965 | Sakuma et al. |
| 3,464,972 A | | 9/1969 | Rocher ..................... 260/210.5 |
| 4,459,285 A | * | 7/1984 | Grollier et al. ............... 424/74 |
| 4,525,411 A | | 6/1985 | Schmidt ..................... 428/198 |
| 4,557,853 A | | 12/1985 | Collins ....................... 252/128 |
| 4,569,839 A | * | 2/1986 | Grollier et al. ............... 424/74 |
| 4,581,230 A | * | 4/1986 | Grollier et al. ............... 424/74 |
| 4,746,510 A | * | 5/1988 | Grollier et al. ............... 424/74 |
| 4,853,281 A | | 8/1989 | Win et al. ................... 428/286 |
| 4,865,221 A | | 9/1989 | Jackson et al. ............... 221/48 |
| 5,006,338 A | | 4/1991 | Luenemann ............. 424/195.1 |
| RE33,993 E | | 7/1992 | Grollier et al. ............... 424/74 |
| 5,607,081 A | | 3/1997 | Levy ........................ 222/83.5 |
| 5,665,392 A | | 9/1997 | Kumar et al. ................ 424/487 |
| 5,872,103 A | | 2/1999 | Belletti ........................ 514/26 |
| 5,939,050 A | * | 8/1999 | Iyer et al. ..................... 424/49 |
| 5,965,165 A | | 10/1999 | Zannini et al. ............. 424/489 |
| 6,159,487 A | * | 12/2000 | Znaiden et al. ............. 424/402 |
| 6,248,343 B1 | * | 6/2001 | Jampani et al. ............. 424/405 |
| 6,436,885 B2 | | 8/2002 | Beidermann et al. ....... 510/131 |
| 2003/0036540 A1 | | 2/2003 | Bomshteyn et al. ........ 514/182 |
| 2003/0064117 A1 | | 4/2003 | Hu et al. .................... 424/725 |
| 2003/0228379 A1 | * | 12/2003 | Shi et al. .................... 424/725 |

FOREIGN PATENT DOCUMENTS

| | | |
|---|---|---|
| DE | 1 088 047 | 9/1960 |
| EP | 552 151 B1 | 3/1997 |
| GB | 759999 | 10/1956 |
| WO | WO/95/096025 | 4/1995 |
| WO | WO/98/00487 | 1/1998 |

OTHER PUBLICATIONS

Field Guide To North American Edible Wild Plants, by Thomas E. Elias and Peter A. Dykeman, published by Outdoor Life Books 1982.

Funk & Wagnalls Standard Dictionary of Folklore Mythology and Legend by Maria Leach and Jerome Fried.

The Concise Herbal Encyclopedia, "Herbs and Health" by Donald Law.

"The Herbalist" by Joseph E. Meyer, 1934.

Clinical and Epidemiologic Principles of Anthrax by Theodore J. Cieslak and Edward M. Eitzen, Jr., U.S. Army Medical Research Institute of Infectius Diseases, Ft. Detrick, Maryland, USA, vol. 5, No. 4, Jul.–Aug. 1988.

From Sugar Lactones to Stereodefined γ–Alkylidenebutenolides—Synthesis of Analogy of the γ–Alkylidenebutenolide Antibiotics Lissoclinolide and Tetrenolin by Felix Christian Gorth, Andras Umland and Reinhard Bruckner, Eur. J. Org. Chem 1988, pp. 1055–1062.

Plant Products As Antimicrobial Agents by Marjorie Murphy Cowan, Clinical Microbiology Reviews, Oct. 1999, p. 564–582.

From Xenobiotic to Antibiotic, Formation of Protoanemonin From 4–Chlorocatechol by Enzymes of the 3–Oxoadipate Pathway by Rafael Blasco, Rolf–Michael Wittich, Medgharaj Malavarapus, Kenneth N. Timmis and Dietmar H. Pieper, The Journal of Biological Chemistry, vol. 270, No. 49, Issue of Dec. 8, pp. 29229–29235.

Minakata et al.; Protoanemonin, an antimutagen isolated from plants; Mutat Res., Mar., 1983;116(3–4): 317–22; PMID: 6339898 [PubMed–indexed for MEDLINE].

Cappelletti et al., External antirheumatic and antineuralogic herbal remedies in the traditional medicine of north–eastern Italy; J Ethnopharmacol; Sep., 1982;6(2):161–90; PMID: 6982378 [PubMed–indexed for MEDLINE].

Mares et al.; Ultrastructural alterations in Epidermophyton floccosum and Trichophyton Mentagrophytes exposed in vitro in protoanemonin; Cytobios. 1990;61(245):89–95; PMID: 2373022 [PubMed–indexed for MEDLINE].

(Continued)

*Primary Examiner*—Necholus Ogden
(74) *Attorney, Agent, or Firm*—Knoble Yoshida & Dunleavy, LLC

(57) ABSTRACT

A anti-microbial composition includes an effective amount of an extract of a plant of the Ranunculaceae family, a surfactant, and optionally an essential oil. To disinfect an object using the anti-microbial composition, the anti-microbial composition is brought into contact with the object. The composition of the invention may be used in the form of packaged towelettes, which are saturated with the composition of the invention. The composition is effective in disinfecting objects contaminated with anthrax, pneumococci, straphylococci, streptococci, tuberculi and a variety of fungi.

23 Claims, No Drawings

OTHER PUBLICATIONS

Mares, D.; Istituto di Botanica dell'Universita di Ferrara, Italy; Electron microscopy of Microsporum cookei after 'in vitro' treatment with protoanemonin: a combined SEM and TEM study; Mycopathologia. Oct., 1989;108(1):37–46; PMID: 2615800 [PubMed–indexed for MEDLINE].

Martin, ML.; Departamento de Fisiologia γ Farmacologia, Universidad de Salamanca, Spain; In vitro study of protoanemonin, an antifungal agent; Planta Med., Feb., 1990 56(1):66–9; PMID: 2356244 [PubMed–indexed for MEDLINE].

Mares et al.; Department of Biology, Section of Botany, University of Ferrara, Italy, Institute of Medical Genetics, University of Ferrara, Italy; Protoanemonin–Induced Cytotoxic Effects IN*Euglena gracilis*; Accepted May 21, 1997.; Available online Apr. 26, 2002.

*The Merck Index; An Encyclopedia of Chemicals, Drugs, and Biologicals*; Twelfth Edition; pp. 108 & 1356; Merck & Co., 1996.

* cited by examiner

ANTI-MICROBIAL COMPOSITIONS

CROSS-REFERENCE TO RELATED APPLICATIONS

This application claims the benefit of U.S. provisional application No. 60/411,329, filed on Sep. 17, 2002, under 35 U.S.C. §119(e).

BACKGROUND OF THE INVENTION

1. Field of the Invention

The invention relates to anti-microbial compositions and methods of using them. More particularly, the present invention relates to an anti-microbial compositions and method of using them to against microbial contamination.

2. Description of the Related Technology

Anti-bacterial cleansing compositions have been widely sold as household products for many years. They are generally used to disinfect household utensils and other household goods. For example, International patent publication WO 95/09605 to Desai discloses a disinfectant cleansing composition containing an alkyl glycoside and a phenolic compound. However, the disinfectant composition of Desai is only disclosed as being effective against common household bacteria such as *E. coli, Staphylococcus aureus* and *Kleb. Pneumoniae.*

Anthrax is resistant to most conventional anti-bacterial compositions. Currently, the primary method to disinfect objects contaminated with anthrax is treating these objects with hazardous chemicals such as chorine dioxide or ozone.

The present invention employs extracts of plant of the Ranunculaceae family. One member of this family of plants, *Ranunculus acris*, has been used to treat headaches by applying the scent of the leaves or juice from the leaves to the nostrils. However, *Ranunculus acris* is generally considered to be toxic and should not be taken internally unless skillfully combined with other plants or ingredients. The juice of *Ranunculus acris* may also cause blisters and it also has been reported that at least one person experienced fever and intense inflammation as a result of the application of a significant quantity of *Ranunculus acris* to the limbs. As a result, little consideration has been given to the potential therapeutic applications of plants of the Ranunculaceae family.

There is still a need for a more effective anti-microbial composition that can disinfect microbial contamination without relying on hazardous chemicals.

SUMMARY OF THE INVENTION

To fulfill the above need, in a first aspect, the present invention provides a composition including an effective amount of an extract of a plant of the Ranunculaceae family; and a surfactant.

In a second aspect, the present invention provides a method of disinfecting an object including the step of contacting the object with a composition comprising an extract of a plant of the Ranunculaceae family.

In other aspects, the present invention provides a variety of products including a substrate; and a solution comprising a surfactant and an extract of a plant of the Ranunculaceae family.

For a better understanding of the invention, its advantages, and the objects obtained by its use, reference should be made to the accompanying descriptive matter, in which there is illustrated and described preferred embodiments of the invention.

DETAILED DESCRIPTION OF THE PREFERRED EMBODIMENT(S)

In a first aspect, the invention provides a composition including an extract of a plant of the Ranunculaceae family, and a surfactant.

Extracts of various plant of the Ranunculaceae family may be employed in the composition of the invention. Particularly suitable plants of the Ranunculaceae family include, but are not limited to, Ranunculus, *Ranunculus acer, Ranunculus acris, Ranunculus apiifolius, Ranunculus aquatilis, Ranunculus arvensis, Ranunculus asiaticus, Ranunculus bulbosus, Ranunculus bullatus, Caltha phylloptera, Clematis aristata, Ranunculus californicus, Ranunculus cantoniensis, Ranunculus cassius, Ranunculus collicola, Ranunculus collinus, Ranunculus communis, Ranunculus creticus, Ranunculus decurvus, Ranunculus falcatus, Ranunculus fascicularis, Ranunculus ficaria, Ranunculus flagelliformis, Ranunculus flammula, Ranunculus glaberrimus, Ranunculus glabrifolius, Ranunculus gunnianus, Ranunculus hiatus, Ranunculus japonicus, Ranunculus lanuginosus, Ranunculus lappaceus, Ranunculus lingua, Ranunculus multifidus, Ranunculus muricatus, Ranunculus nanus, Ranunculus occidentalis, Ranunculus parnassifolius, Ranunculus parviflorus, Ranunculus pascuinus, Ranunculus pennsylvanicus, Ranunculus petiolaris, Ranunculus pimpinellifolius, Ranunculus pinnatus, Ranunculus pubescens, Ranunculus pumilio, Ranunculus pusillus, Ranunculus repens, Ranunculus rivularis, Ranunculus scapiger, Ranunculus sceleratus, Ranunculus* sp, *Ranunculus stoloniferus, Ranunculus sylvestris, Ranunculus trichophyllus, Ranunculus triplodontus* and *Ranunculus zuccarinii*. In a preferred embodiment, the plants of the Ranunculaceae family employed to provide an extract useful in the present invention are selected from *Ranunculus acris, Ranunculus bulbosus, Ranunculus sceleratus* and *Ranunculus*. In a most preferred embodiment, the plant of the Ranunculaceae family employed to provide an extract useful in the present invention is *Ranunculus acris*. Plants of the Ranunculaceae family are often referred to as buttercups or crowfoot. Also, plants from the order Ranunculaceae such as *Anemone Pulsatilla* and *Anemone pratensis* can also be employed if such plants include anemonin.

*Ranunculus acris* may also be referred to by one or more of the following common names, ranunculus bulbous, buttercup bulbous, upright meadow crowfoot, marsh crowfoot, frogsfoot, St. Anthony's turnip, gold cup, jaunet (in French), greater celandine, lessor celandine, lessor spearwort, barrakion (in Greek), gold knob, king's knob, baffingers, triolflowers, polts, locket goulons, butter flowers, blister flowers and yellow weed.

An extract of a plant of the Ranunculaceae family may be prepared using any suitable, well-known extraction method. Such extraction methods are within the common general knowledge of skilled persons. For example, an exemplary extraction method includes the steps of:

1) cleaning the plant to remove any foreign matter thereon;

2) particulating the plant to obtain a particulate mass having particle size ranging from 0.001 to about 10 $mm^3$; and 3) contacting the particulate mass with at least one suitable solvent to obtain one or more separate fractions of the plant extract soluble in the at least one solvent, and 4) mixing the fraction so obtained to obtain a plant extract.

For instance, in the case of a buttercup plant such as *Ranunculus acris*, the method may include some or all of the steps of:

1) cleaning the buttercup plant to remove any foreign matter thereon;

2) particulating the plant to obtain a particulate mass having particle size ranging from 0.001 to about 10 mm$^3$;

4) cooking or steeping the particulate mass in a first solvent, such as water to solubilize material in the particulate mass to obtain a first solution and a first residue; and 5) filtering the first solution from the first residue and using the first solution as the extract in the composition of the invention.

Alternatively, the first solution and first residue may be subjected to the additional processing steps listed below:

6) evaporating the filtrate obtained from the first solution to remove the solvent and obtain a solute designated as fraction A from the particulated mass;

7) subjecting the first residue to treatment with a second solvent such as 75% to 95% ethanol for twelve to thirty-six hours to obtain a second solution and a second residue;

8) filtering the second solution from the second residue to obtain a second filtrate;

9) evaporating the second filtrate to remove its solvent and obtain a solute designated as fraction B from the particulated mass;

10) subjecting the second residue to a third solvents; such as petroleum ether, for twelve to thirty-six hours to obtain a third solution and a third residue, and filtering the third solution from the third residue to obtain a third filtrate;

11) evaporating the third filtrate to remove its solvent and obtain a solute designated as fraction C from the particulated mass; and 12) homogeneously mixing the fractions A, B and C from the particulated mass to obtain a beneficiated plant extract.

In a preferred embodiment, to produce an extract from *Ranunculus acris* in the form of a decoction, 4 ounces of buttercup plant is mixed with 16 ounces of water or another liquid to form a mixture. The mixture is heated to a boil for about 5–10 minutes, removed from the heat and allowed to steep for 10–15 minutes for soft materials and 15–30 minutes for hard materials such as stems, roots, or bark. It is preferable to carry out this process in a non-metallic container. The liquid portion of the mixture is then separated and directly used as the extract of the buttercup plant without further processing or evaporating the water contained therein.

Alternatively, if it is desirable to minimize the loss of volatiles from the plant, an infusion can be prepared by, for example, bringing 16 ounces of water to a boil, preferably in a non-metallic container, removing the water from the heat and adding 4 ounces of plant to the boiling water, covering the mixture and allowing the covered mixture to steep for 15–30 minutes for soft materials and 30–60 minutes for hard materials. The plant is then strained off to leave a liquid infusion from the plant, which has a higher content of the plant volatiles than the decoction described above.

A cold extract can be prepared by mixing eight ounces of plant with 10 ounces of water or liquid, allowing the mixture to sit for 8–24 hours and straining the mixture. A cold extract will preserve volatile elements of the plant but will extract only a minimal amount of salt and bitter elements. Other types of herbal preparations that may be employed can be found, for example, in *The Herb Book*, Lust, John, pp. 36∝41, Bantam Books (1975), the disclosure of which is hereby incorporated by reference for the purpose of describing how to make and use herb preparations.

The extract of the present invention may also be prepared by synthetic methods by first identifying one or more of the active compounds in an extract of a plant of the Ranunculaceae family and then applying a suitable synthetic method to produce the one or more active compounds. Thus, the present invention contemplates use of various synthetic methods to provide an extract of a plant of the Ranunculaceae family including chemical synthesis, and biological synthesis methods. Also mixtures of synthetic materials and plant extracts may also be employed to, for example, fortify one or more active ingredients of the plant extract.

For example, it is considered that one or more of anemonin, protoanemonin and diterpenoid alkaloids may be important constituents in the extracts obtained from plants of the Ranunculaceae family. Various synthesis methods for making these compounds are known to persons skilled in the art and thus can be used to provide an extract in accordance with the present invention.

An extract in the form of juice can be prepared by chopping the fresh plants and/or plant parts into small pieces and pressing to squeeze out the juices. The extraction can be repeated and it may be useful to add a small amount of water to the pressed plant before pressing again. This method is best for extracting the water-soluble elements that are sensitive to heat and or drying in addition to the vitamins and minerals. The juice must be used relatively promptly to avoid loss of essential contents and/or fermentation of the juice, or a natural preservative as benzoin could be added to the juice to increase its shelf life. Caution should be exercised in working with the fresh plant since it may be an irritant.

A powder extract can be prepared by drying the entire plant, preferably under low light and in a well-ventilated area. Leaves should preferably be dried on the stems. The dried plants and stems may then be ground by, for example, using mortar and pestle or other suitable implements, until they are reduced to a powder. The powder extract can be used in tinctures, poultices as well as ointments, or the powder extract can be formulated into other types of compositions.

An ointment can be prepared by, for example, mixing one part of the powdered plant to four parts of petroleum jelly or any other suitable carrier for an ointment. Alternatively, an ointment can be prepared by boiling the plant in water to remove volatiles by decoction, straining the water off, and adding the liquid decoction to olive oil, another suitable vegetable oil or any other ointment base. If added to an oil base, it is preferably to simmer until all water has been evaporated and add a thickener such as beeswax, as needed, to obtain a firm consistency.

The mixture may then be melted slowly over low heat, stirred until completely blended and a preservative, such as gum of benzoin or a drop of the tincture of benzion per ounce of oil, may be added to help preserve the ointment.

A poultice may be used to apply a remedy to the skin area with moist heat. To prepare a suitable poultice, crush or bruise the plant to a pulpy mass and heat. If using the dried plant a moistened binder such as flour, corn starch, cornmeal and water or milk, may be used to formulate the poultice. The poultice can be applied directly to the skin or can be spread between two pieces of cloth, moistened and heated and applied to the area desired. The poultice can be used to soothe, irritate, or to draw impurities out of the body, in addition to providing the beneficial effects of the present invention.

The surfactant employed in the composition of the invention may be any surfactant that may suitably be employed in soaps, household cleansing compositions or detergent compositions. Exemplary surfactants that may be employed in the composition of the present invention may include synthetic detergents, soaps, fatty acid salts, alkyl ether carboxylates, alkyl ethoxylates, alkyl ether sulfates and sulfonates, alkyl sulfates and sulfonates, alkylbenzene sulfonates, quaternary ammonium compounds, other anionic, nonionic, zwitterionic and amphoteric surfactants, and mixtures thereof.

The synthetic detergents can be selected from the anionic, nonionic, amphoteric and ampholytic types. Such detergents are well known to those skilled in the detergency art. The most common type of anionic synthetic detergents can be broadly described as the water-soluble salts, particularly the alkali metal salts, of organic sulfuric reaction products having in the molecular structure an alkyl radical containing from about 8 to about 22 carbon atoms and a radical selected from the group consisting of sulfonic acid and sulfuric acid ester radicals. Important examples of these synthetic detergents are the sodium, ammonium or potassium alkyl sulfates, especially those obtained by sulfating the higher alcohols produced by reducing the glycerides of tallow or coconut oil; sodium or potassium alkyl benzene sulfonates, in which the alkyl group contains from about 9 to about 15 carbon atoms, especially those of the types described in U.S. Pat. Nos. 2,220,099 and 2,477,383, incorporated herein by reference; sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid esters of the reaction product of one mole of a higher fatty alcohol (e.g., tallow or coconut oil alcohols) and about three moles of ethylene oxide; sodium or potassium salts of alkyl phenol ethylene oxide ether sulfates with about four units of ethylene oxide per molecule and in which the alkyl radicals contain about 9 carbon atoms; the reaction product of fatty acids esterified with isethionic acid and neutralized with sodium hydroxide where, for example, the fatty acids are derived from coconut oil; sodium or potassium salts of fatty acid amide of a methyl taurine in which the fatty acids, for example, are derived from coconut oil; and others known in the art, a number being specifically set forth in U.S. Pat. Nos. 2,486,921, 2,486,922 and 2,396,278, incorporated herein by reference.

Nonionic synthetic detergents comprise a class of compounds which may be broadly defined as compounds produced by the condensation of alkylene oxide groups (hydrophilic in nature) with an organic hydrophobic compound, which may be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

For example, a well-known class of nonionic synthetic detergents is made available on the market under the trade name of "Pluronic." These compounds are formed by condensing ethylene oxide with an hydrophobic base formed by the condensation of propylene oxide with propylene glycol. The hydrophobic portion of the molecule which, of course, exhibits water-insolubility has a molecular weight of from about 1500 to 1800. The addition of polyoxyethylene radicals to this hydrophobic portion tends to increase the water-solubility of the molecule as a whole and the liquid character of the products is retained up to the point where polyoxyethylene content is about 50% of the total weight of the condensation product.

Other suitable nonionic synthetic detergents include:

(i) The poyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 25 moles of ethylene oxide per mole of alkyl phenol. The alkyl substituent in such compounds may be derived from polymerized propylene, diisobutylene, octane, and nonane, for example.

(ii) Those derived from the condensation of ethylene oxide with the product resulting from the reaction of propylene oxide and ethylene diamine—products which may be varied in composition depending upon the balance between the hydrophobic and hydrophilic elements which is desired. Examples are compounds containing from about 40% to about 80% polyoxyethylene by weight and having a molecular weight of from about 5000 to about 11,000 resulting from the reaction of ethylene oxide groups with a hydrophobic base constituted of the reaction product of ethylene diamine and excess propylene oxide, said base having a molecular weight of the order of 2500 to 3000, are satisfactory.

(iii) The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

(iv) Trialkyl amine oxides and trialkyl phosphine oxides wherein one alkyl group ranges from 10 to 18 carbon atoms and two alkyl groups range from 1 to 3 carbon atoms; the alkyl groups can contain hydroxy substituents; specific examples are dodecyl di(2-hydroxyethyl) amine oxide and tetradecyl dimethyl phosphine oxide.

Zwitterionic detergents comprise the betaine and betaine-like detergents wherein the molecule contains both basic and acidic groups which form an inner salt giving the molecule both cationic and anionic hydrophilic groups over a broad range of pH values. Some common examples of these detergents are described in U.S. Pat. Nos. 2,082,275, 2,702, 279 and 2,255,082, incorporated herein by reference. Suitable zwitterionic detergent compounds have the formula ##STR1## wherein $R^1$ is an alkyl radical containing from about 8 to about 22 carbon atoms, $R^2$ and $R^3$ contain from 1 to about 3 carbon atoms, $R^4$ is an alkylene chain containing from 1 to about 3 carbon atoms, X is selected from the group consisting of hydrogen and a hydroxyl radical, Y is selected from the group consisting of carboxyl and sulfonyl radicals and wherein the sum of the $R^1$, $R^2$ and $R^3$ radicals is from about 14 to about 24 carbon atoms.

Amphoteric and ampholytic detergents which can be either cationic or anionic depending upon the pH of the system are represented by detergents such as dodecyl-beta-alanine, N-alkyltaurines such as the one prepared by reacting dodecylamine with sodium isethionate according to the teaching of U.S. Pat. No. 2,658,072, N-higher alkylaspartic acids such as those produced according to the teaching of U.S. Pat. No. 2,438,091, and the products sold under the trade name "Miranol," and described in U.S. Pat. No. 2,528,378, said patents being incorporated herein by reference.

Additional synthetic detergents and listings of their commercial sources can be found in McCutcheon's Detergents and Emulsifiers, North American Ed. 1980, incorporated herein by reference.

Soaps which can be used as the surfactant in the present compositions are alkali metal (e.g., sodium or potassium) soaps of fatty acids containing from about 8 to about 24, preferably from about 10 to 20 carbon atoms. The fatty acids used in making the soaps can be obtained from natural sources such as, for instance, plant or animal-derived glycerides (e.g., palm oil, coconut oil, babassu oil, soybean oil, castor oil, tallow, whale oil, fish oil, tallow, grease, lard and mixtures thereof). The fatty acids can also be synthetically prepared (e.g., by oxidation of petroleum stocks or by the Fischer-Tropsch process).

Alkali metal soaps can be made by direct saponification of the fats and oils or by the neutralization of the free fatty acids which are prepared in a separate manufacturing process. Particularly useful are the sodium and potassium salts of the mixtures of fatty acids derived from coconut oil and tallow, i.e., sodium and potassium tallow and coconut soaps.

The term "tallow" is used herein in connection with fatty acid mixtures which typically have an approximate carbon chain length distribution of 2.5% C.sub. 14, 29% C.sub. 16, 23% C.sub. 18, 2% palmitoleic, 41.5% oleic and 3% linoleic (the first three fatty acids listed are saturated). Other mixtures with similar distribution, such as the fatty acids derived from various animal tallows and lard, are also included within the term tallow. The tallow can also be hardened (i.e., hydrogenated) to convert part or all of the unsaturated fatty acid moieties to saturated fatty acid moieties.

When the term "coconut oil" is used herein it refers to fatty acid mixtures which typically have an approximate carbon chain length distribution of about 8% C.sub.8, 7% C.sub.10, 48% C.sub.12, 17% C.sub.14, 9% C.sub.16, 2% C.sub.18, 7% oleic, and 2% linoleic (the first six fatty acids listed being saturated). Other sources having similar carbon chain length distribution such as palm kernel oil and babassu oil are included with the term coconut oil.

Exemplary alkyl ether carboxylates include alkyl ethoxy carboxylates having the following general formula:

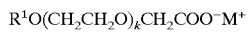

wherein $R^1$ is a straight or branched hydrocarbon chain, preferably, a $C_{10}$ to $C_{22}$ alkyl or alkenyl group, k ranges from about 2 to about 7, and $M^+$ is a water-solubilizing cation such as an alkali metal, alkaline earth metal, ammonium ion or a mixture thereof.

Exemplary alkyl ethoxylates have the following general formula:

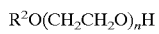

wherein $R^2$ is a straight or branched hydrocarbon chain, preferably, a $C_{10}$ to $C_{22}$ alkyl or alkenyl group, and n ranges from about 2 to about 7.

Exemplary alkyl sulfates have the following general formula:

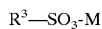

wherein $R^3$ is a straight or branched hydrocarbon chain, preferably, a $C_8$ to $C_{22}$ alkyl or alkenyl group, and M is a water-solubilizing cation such as an alkali metal, alkaline earth metal, ammonium ion, or a mixture thereof.

The anti-microbial compositions of the present invention comprise an amphoteric surfactant at concentrations ranging from about 0.01% to about 20%, preferably from about 0.05% to about 10%, more preferably from 0.05% to about 10%, by weight of the composition.

Amphoteric surfactants useful in the present invention are those having the following general formulae (I) (II), (III), (IV) and (V) and mixtures thereof:

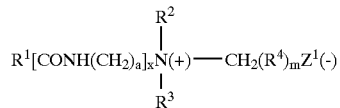

wherein $R^1$ is an alkyl, alkenyl, aryl, or hydroxyalkyl radical of from about 8 to about 22 carbon atoms, optionally interrupted with up to about 10 ethylene oxide moieties and/or 1 glyceryl moiety, $R^2$ and $R^3$ are individually selected from alkyl and monohydroxyalkyl groups containing from about 1 to about 3 carbon atoms, $R^4$ is alkylene, or hydroxyalkylene of from about 1 to about 4 carbon atoms, $Z^1$ is a radical selected from carboxylate, sulfonate, sulfate, phosphate, or phosphonate, x is 0 or 1, n is from about 1 to about 6, and m is 0 or 1. Preferably, $R^1$ is an alkyl, alkenyl, or hydroxyalkyl radical of from 11 to 17 carbon atoms, $R^2$ and $R^3$ are individually selected from alkyl groups containing of from 1 to 3 carbon atoms, $R^4$ is alkylene or hydroxyalkylene of from 1 to 2 carbon atoms, $Z^1$ is a radical selected from carboxylate and sulfonate, x is 0 or 1, n is 1 to 3, and m is 0 or 1.

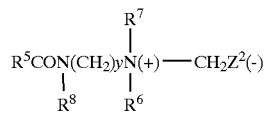

wherein $R^5$ is $C_8$–$C_{22}$ alkyl, alkenyl, aryl, or hydroxyalkyl, $R^6$ is hydrogen or $CH_2CO_2M^1$, $R^7$ is $CH_2CH_2OH$ or $CH_2CH_2OCH_2COOM^1$, $R^8$ is hydrogen, $CH_2CH_2OH$ or $CH_2CH_2OCH_2COOM^1$, $Z^2$ is $CO_2M$ or $CH_2CO_2M^1$, y is 2 or 3, $M^1$ is hydrogen or a cation, such as alkali metal, alkaline earth metal, ammonium, alkanol ammonium, sulfate, sulfonate, phosphate, or phosphonate.

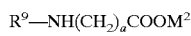

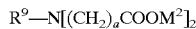

wherein a is a number from 1 to 4, $R^9$ is $C_8$–$C_{22}$ alkyl, alkenyl, aryl, hydroxyalkyl or alkylamidoalkyls, and $M^2$ is hydrogen, alkali metal, alkaline earth metal, ammonium or alkanolammonium.

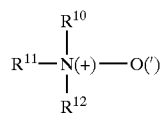

wherein $R^{10}$ or $R^{12}$ is methyl, ethyl, or hydroxyethyl, and $R^{11}$ is $C_8$–$C_{22}$ alkyl, alkenyl, or aryl, or $CH_3(CH_2)pCONH(CH_2)q$, wherein p is 8–22 and q is 1–6. Preferably, $R^{10}$ and $R^{12}$ are methyl, $R^{11}$ is $C_{10-18}$ alkyl or alkenyl, p is 11–17, and q is 1–3.

Examples of amphoteric surfactants useful in the anti-microbial compositions having general formula (I) are amide betaines, amide sulfo betaines, alkyl betaines, alkenyl betaines, sultaines(sulfo betaines), and imidazolinium betaines. Examples of amphoteric surfactants particularly useful are high alkyl betaines, such as coco dimethyl carboxymethyl betaine, cocamidopropyl betaine under the trade name of TEGO BETAINE, coco betaine, lauryl betaine under the trade name REWOTERIC AM DML-35, lauryl amidopropyl betaine, oleyl betaine, lauryl dimethyl carboxymethyl betaine, lauryl dimethyl alpha-carboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl)alpha-carboxyethyl betaine, cocamidopropyl hydroxy sultaine(sulfobetaine), lauryl sultaine(lauryl sulfobetaine), and cocamidopropryl hydroxy sultaine under the trade name REWOTERIC AM CAS.

Examples of amphoteric surfactants useful in the anti-microbial compositions having general formula (II) are marketed under the trade name MIRANOL and are understood to comprise a complex mixture of species, and can exist in protonated and non-protonated species depending upon pH with respect to species that can have a hydrogen at R.sup.6. The imidazolinium amphoteric surfactant hereof can be derived via an imidazolinium intermediate.

Preferred amphoteric surfactants of formula (II) are monocarboxylates and dicarboxylates. Examples of these materials include cocoamphocarboxypropionate, cocoamphocarboxypropionic acid, cocoamphocarboxyglycinate (alternately referred to as cocoamphodiacetate), and cocoamphoacetate.

Specific commercial products providing the imidazolinium derivative component of the present compositions include those sold under the trade names MIRANOL C2M CONC. N.P., MIRANOL C2M CONC. O.P., MIRANOL C2M SF, MIRANOL CM SPECIAL (Miranol, Inc.); ALKATERIC 2CIP (Alkaril Chemicals); cocoamphocarboxy propionate under the trade name NIKKOL AM-101, AMPHOTERGE W-2 (Lonza, Inc.); MONATERIC CDX-38, MONATERIC CSH-32 (Mona Industries); REWOTERIC AM-2C (Rewo Chemical Group); and SCHEROTERIC MS-2 (Scher Chemicals).

Examples of amphoteric surfactants useful in the anti-microbial compositions having general formulae (III) and (IV) include n-alkylaminopropionates and n-alkyliminodipropionates. Such materials are sold under the trade name DERIPHAT by Henkel and MIRATAINE by Miranol, Inc. Specific examples include N-lauryl-beta-amino propionic acid or salts thereof, and N-lauryl-beta-imino-dipropionic acid or salts thereof.

Examples of amphoteric surfactants useful in the anti-microbial compositions having general formula (V) are commonly known as amine oxides. Also useful are tertiary phosphine oxides and dialkyl sulfoxides. Mixtures of the above amphoteric surfactants can also be used.

The most preferred amphoteric surfactants are amine oxides. Examples of amine oxides particularly useful in the anti-microbial compositions are cocamine oxide, lauramine oxide under the trade name AMMONYX LO, and stearamidopropylamine oxide under the trade name VAROX 1770.

In a preferred embodiment, the surfactant employed in the invention is a detergent composition, a soap or a mixture of soaps.

In a preferred embodiment, the composition of the invention may further include an essential oil. In one embodiment, the essential oil that may be included in the composition of the invention may be an essential oil that has antiseptic properties. Exemplary essential oils that have antiseptic properties include tea tree oil, thyme oil, pine oil, and peppermint oil. In another embodiment, the essential oil that may be included in the composition of the invention may be an essential oil that can facilitate dispersion or dissolution of natural body oil, excretions associated with infection, lymph, lumps of white blood cells, and/or pus. An exemplary essential oil that can facilitate dispersion or dissolution of pus is tea tree oil.

In a more preferred embodiment, the essential oil used in the invention is tea tree oil, which is an essential oil of *Melaleuca alternifolia*. Tea tree oil is readily available from many commercial sources. Tea tree oil is the oil that is found within the cells of the leaves of tea trees. Clinical trials have confirmed that tea tree oil has anti-fungal, antiseptic, germicidal and anti-microbial properties. Additionally, the antiseptic benefits of the tea tree oil allow its use as a natural cleaner and disinfectant in a household environment. As mentioned above, tea tree oil is also effective in dissolving and dispersing lumps of white blood cells or pus to reduce or eliminate infections without significantly irritating or damaging the surround tissues, thereby facilitating wound healing with minimal scarring.

Generally, the ingredients of the composition of the present invention, including a surfactant, an extract from a plant of the Ranunculaceae family, and optionally an essential oil, are combined at effective ratios. In one embodiment, the composition of the invention contains 50–99 wt. % of surfactant, based on the total dry weight of the composition. "Dry weight" is generally defined as the weight when the composition or ingredients are substantially free of water or moisture. In this embodiment, about 0.2 oz. to about 5 oz. of an extract of a plant of the Ranunculaceae family is included in every 10 oz. of the composition of the present invention, based on dry weight. In a preferred embodiment, every 10 oz. of the composition, based on dry weight, contains from about 0.1 oz. to 0.5 oz. of tea tree oil and about 0.8 oz. to about 2 oz. of an extract of *Ranunculus acris*, with the bulk of the remainder of the composition being soap.

Depending on the ultimate purpose of the composition, the composition of the invention may include other optional ingredients such as other anti-microbial agents, builders, foam-forming agent, fluorescent brightening agent, solvent, shampoo, coloring agents, thickening agents, polymeric conditioning agents, oil-derived nonionic surfactants, fragrances, cosmetic oils or waxes, skin moisturizing agents, preservatives, free fatty acids such as coconut oil fatty acid, dyes, pigments, vegetable starches such as corn, potato, rice and tapioca starches, or a mixture of two or more of these additional optional ingredients.

Representative thickening agents may include one or more of hydroxyethyl cellulose, hydroxylpropyl cellulose, hydroxypropyl methyl cellulose, polyethylene glycol, polyacrylamide, polyacrylic acid, polyvinyl alcohol, polyvinyl pyrrolidone, dextrans, carboxymethyl cellulose, plant exudates such as acacia, xanthan, ghatti, and tragacanth, seaweeds extracts such as sodium alginate, propylene glycol alginate and sodium carrageenan, acrylic acid/ethyl acrylate copolymers and carboxyvinyl polymers.

Representative polymeric conditioning agents include cationic polysaccharides; cationic homopolymers and copolymers derived from acrylic and/or methacrylic acid; cationic cellulose resins; cationic copolymers of dimethyldiallylammonium chloride and acrylamide and/or acrylic acid; cationic honopolymers of dimethyldiallylammonium chloride; cationic polyalkene and ethoxypolyalkene imines; quaternized silicones, and mixtures thereof.

Suitable oil derived nonionic surfactants may include one or more of water soluble vegetable and animal-derived emollients such as triglycerides with a polyethyleneglycol chain inserted; ethoxylated mono and di-glycerides, polyethoxylated lanolins and ethoxylated butter derivatives.

Suitable cosmetic oils and waxes may be selected from water-insoluble silicones, $C_1$–$C_{24}$ esters of $C_8$–$C_{30}$ fatty acids, $C_8$–$C_{30}$ esters of benzoic acid, beeswax, saturated and unsaturated fatty alcohols, hydrocarbons such as mineral oils, petrolatum squalane, animal and vegetable triglycerides and $C_1$–$C_{24}$ esters of dimmer and trimer acids.

Suitable skin moisturizing agents may include nonionic water-soluble cellulose ethers such as methyl cellulose, hydroxypropyl methyl cellulose, hydroxyethyl cellulose, hydroxylpropyl cellulose, ethyl hydroxyethyl cellulose, polybutene, squalane, sodium pyrrolidone carboxylic acid, D-panthenol, lactic acid, L-proline, guanidine, pyrrolidone, hydrolyzed protein and other collagen-derived proteins, aloe vera gel, acetamide MEA and lactamide MEA and mixtures thereof.

Suitable preservatives may include one or more of DMDM Hydantoin, Germall 115, methyl, ethyl, propyl and butyl esters of hydroxybenzoic acid, EDTA, Euxyl (RTM) K400, natural preservatives such as benzyl alcohol, potassium sorbate and bisabalol; sodium benzoate and 2-phenoxylethanol.

The anti-microbial composition of the invention can be employed in health care, personal care, home care, e.g. for cleaning surfaces, in the textile industry, in food or chemical manufacturing or processing facilities, in the tanning and hide industries, in agriculture and for environmental protection or reclamation, for example. For these various purposes, the anti-microbial composition of the invention can be formulated into many different forms such as a liquid anti-microbial soap, a waterless anti-microbial soap, a skin cleanser, a surgical scrub, a cleansing composition contained in tissues, towelettes, wipes, swabs, sponges, packs, hand sanitizers, facial protectors and other protective apparel such as gloves and suits used for decontamination, a liquid anti-microbial spray, pump spray or aerosol, a liquid anti-microbial concentrate, an anti-microbial aerosol spray, a sterilizing solution, an all-purpose cleansing detergent, and bar soap. The anti-microbial composition of the invention can also be employed for wound care, topical skin care, and oral care. Common procedures, such as molding into a soap bar, powderizing the composition, or diluting the composition with suitable solvents or dispersants, such as deionized water, may be used to produce the above-mentioned forms of anti-microbial compositions based on the composition of the invention.

Other products may include shampoos, rinses, hair conditioners, bath products such as, for example, beads or oils and lotions which can be used as a protective measure prior to exposure to microbes or as a treatment after exposure to the microbes. The composition of the present invention can also be incorporated into laundry detergents of all types including powders, liquids, gels and tablets, fabric care additives used in laundering fabrics, dishwashing detergents for use by hand or with dishwashing machines, toilet and bathroom cleaners such as tub, tile and sink cleaners, abrasive cleaners, all purpose cleaning products, glass and other surface cleaners, as well as carpet shampoos, upholstery cleaners and treatments and animal cleaning products. The composition of the invention can also be used in salves and ointments, including over-the-counter products. In addition, the composition of the invention can be used in diapers such as, including training diapers, youth diapers, swim diapers, adult incontinence products and feminine hygiene products. Also, surgical drapes and gowns and sterile wraps may contain the composition of the present invention.

The present invention also encompasses a variety of products as mentioned above containing a composition of the invention. These products contain a substrate and have an anti-microbial composition of the invention absorbed or dispersed therein, or associated therewith. The product may be immersed in a solution of the anti-microbial composition of the invention for a suitable amount of time (e.g., between 1 minute to 1 hour) to absorb an effective amount of the composition. The product is preferably saturated with a solution of the anti-microbial composition of the present invention. In one embodiment, the various products of the invention mentioned above may include only the extract of a plant of the Ranunculaceae family, optionally in the form of a solution or a powder. In an alternative embodiment, the various products of the invention mentioned above may include the extract of a plant of the Ranunculaceae family in combination with a surfactant, as described in detail above.

The individual products may be sheets, towels, wipes, swabs, sponges, tissues, etc. made from cellulosic fibers, or non-woven products made from synthetic polymers such as polypropylene, polyethylene, polymethyl pentene, other polyolefins, polyesters such as poly(ethylene terephthalate), poly(butylenes terephthalate) and polycaprolactam. In a preferred embodiment, the products used in the invention are microporous or contain microporous fibers so that their absorbing efficiency is improved.

The anti-microbial composition of the invention may be diluted to a suitable concentration with water for absorption onto the products. The ideal concentration of such a solution depends on the ultimate purpose of the products and can be suitably adjusted by a person of ordinary skill in the art using common general knowledge. Alternatively, the anti-microbial compositions of the present invention can be dried to a powder form and associated with the various products mentioned above in powder form, if desirable.

The individual products generally contain from about 1 to 1000 wt. %, based on the dry weight of the products, of a solution containing a composition of the invention. More preferably, the products contain from about 10 to about 500 wt % , of a solution containing a composition of the invention, based on the dry weight of the products, depending primarily on the concentration of the solution, and most preferably from about 100 to about 300 wt %. The products may be individually packaged in sealed packs, or packed as a group in, for example, a re-sealable a plastic container.

To disinfect an object, which is contaminated or potentially contaminated with undesirable or hazardous microorganisms, the composition of the present invention is brought in contact with the object. In one embodiment, a spray containing the composition of the invention is applied to the surface of a contaminated object to disinfect the object. In another embodiment, a towelette of the invention is used to wipe the surface of a contaminated object to disinfect the object. In yet another embodiment, the extract of the Ranunculaceae family plant can be directly applied to an object for the purpose of disinfection. Any type of extract including infusion, cold extract, powder, decoction, etc. may be employed for this purpose. Alternatively, a formulation, such as an ointment or tincture, may be employed for disinfection.

Objects which may require disinfection include, but are not limited to, air filters, air conditioning systems, ventilation systems, heating systems, gas masks, mass transportion such as buses, trains, planes, etc, public places like restaurants, hotel rooms, building lobbies, places of employment, etc. Also, the present invention can be used in areas where there are hoofed animals such as farms, farm or grazing soils, and slaughterhouses.

The compositions of the present invention, and/or the extract of the Ranunculaceae family plant may also be embedded in, for example, a filter or other similar device and be used to treat filtered air, water, or the like to provide the anti-microbial or anti-microbial effect.

The composition of the invention appears to be effective in exterminating or eliminating a variety of hazardous microorganisms at concentration levels that are safe for use in human or animal environments including bacteria, fungi and other microbes. Those microorganisms that can be disinfected using the composition include, for example, anthrax, pneumococci, straphylococci, streptococci, tuberculi and a variety of fungi. In addition, tests have shown that the composition of the invention maybe handled with bare hands and may be used as an anti-microbial hand-cleansing agent at effective concentrations without posing an unacceptable risk to the user of the composition.

The composition of the present invention is preferably used in amounts that deliver at least about 2 ppm of anemonin, protoanemonin, diterpenoid alkaloids, or combinations thereof, more preferably, at least about 5 ppm of anemonin, protoanemonin, diterpenoid alkaloids, or combinations thereof, and most preferably at least about 15 ppm of anemonin, protoanemonin, diterpenoid alkaloids, or combinations thereof. It has been found that amounts that deliver 25-200 ppm of, for example, protoanemonin, are generally bactericidal for a variety of common bacteria.

Alternatively, the amount used can be determined based on the extract itself. For example, it is preferably to deliver a minimum inhibitory concentration of 1.0 micrograms per milliliter, and more preferably, a minimum inhibitory concentration of from about 1.0 to about 20.0 micrograms per milliliter, even more preferably, 1.5 to about 15 micrograms per milliliter. The minimum inhibitory concentration was determined using the dilution assay method.

The upper limit of the amount of the composition of the present invention will depend upon how the extract is made and may be determined by the levels at which toxicity or irritation becomes an issue. Thus, for surface cleansers, very high concentrations can be employed, whereas for skin cleansers, oral care or other products used for direct contact with humans or animals, lower concentrations will be desirable to avoid irritation or toxicity issues. For example, it has been found that dosages of protanemonin of 190 mg/kg in a mouse reach the $LD_{50}$ limit and dosages of anemonin of 150 mg/kg in a mouse reach the $LD_{50}$ limit and thus such high concentrations should be avoided when contact with humans or animals is expected. Use of the term, "safe amount" herein refers to concentrations which are sufficiently below the above-mentioned amounts to avoid toxic effects in humans or animals.

In addition, certain preferred compositions of the invention may act as a solvent to dissolve the lumps of white blood cells, which make pus. In fact, the composition of the invention may also be useful as an antibiotic agent to be applied to an injured or infected area to help prevent or eliminate infection.

The invention will be further illustrated by the following non-limiting example.

EXAMPLES

Example 1

Preparation of Anti-Microbial Composition

In a non-metallic container, 4 oz. of buttercup plant (*Ranunculus acris*) was mixed with 16 oz. of water. The resulting mixture of herb and water was heated to a boil, boiled for about 5–10 minutes, removed from the heat, and steeped in the water for about 15–30 minutes to form a solution containing an extract of the buttercup. ⅓ cup of the solution containing the buttercup extract was then added to 16 ounces of soap base and mixed thoroughly to form an anti-microbial composition of the invention.

Example 2

Preparation of Anti-Microbial Composition

To the composition of Example 1 was added and ⅔ oz. of tea tree oil to prepare a second anti-microbial composition in accordance with the present invention.

It is to be understood that the foregoing detailed description is given merely by way of illustration and that many variations may be made within the principles of the invention to the full extent indicated by the broad general meaning of the terms in which the appended claims are expressed.

What is claimed is:

1. A anti-microbial composition comprising:
   an anti-microbially effective amount of an extract of a plant selected from the group consisting of: *Ranunculus, Ranunculus acer, Ranunculus acris, Ranunculus apiifolius, Ranunculus aquatilis, Ranunculus arvensis, Ranunculus asiaticus, Ranunculus bulbosus, Ranunculus bullatus, Caltha phylloptera, Clematis aristata, Ranunculus californicus, Ranunculus cantoniensis, Ranunculus cassius, Ranunculus collicola, Ranunculus collinus, Ranunculus communis, Ranunculus creticus, Ranunculus decurvus, Ranunculus falcatus, Ranunculus fascicularis, Ranunculus ficaria, Ranunculus flagelliformis, Ranunculus flammula, Ranunculus glaberrimus, Ranunculus glabrifolius, Ranunculus gunnianus, Ranunculus hiatus, Ranunculus japonicus, Ranunculus lanuginosus, Ranunculus lappaceus, Ranunculus lingua, Ranunculus multifidus, Ranunculus muricatus, Ranunculus nanus, Ranunculus occidentalis, Ranunculus parnassifolius, Ranunculus parviflorus, Ranunculus pascuinus, Ranunculus pennsylvanicus, Ranunculus petiolaris, Ranunculus pimpinellifolius, Ranunculus pinnatus, Ranunculus pubescens, Ranunculus pumilio, Ranunculus pusillus, Ranunculus repens, Ranunculus rivularis, Ranunculus scapiger, Ranunculus sceleratus, Ranunculus sp, Ranunculus stoloniferus, Ranunculus sylvestris, Ranunculus trichophyllus, Ranunculus triplodontus, Ranunculus zuccarinii, Anemone pulsatilla* and *Anemone pratensis*; and
   a surfactant.

2. An anti-microbial composition as claimed in claim 1, wherein said plant is *Ranunculus acris*.

3. A anti-microbial composition as claimed in claim 1 further comprising an essential oil.

4. A anti-microbial composition as claimed in claim 3, wherein said essential oil is tea tree oil.

5. A anti-microbial composition as claimed in claim 4, wherein between 0.1 oz. to 0.5 oz. of said tree oil is included in every 10 oz. of said composition, based on dry weight.

6. A anti-microbial composition as claimed in claim 1, wherein said surfactant is soap.

7. A anti-microbial composition as claimed in claim 1, wherein an equivalence of said extract of between 0.2 oz. and 5 oz. of said plant is included in every 10 oz. of said composition, based on dry weight.

8. A anti-microbial composition as claimed in claim 1, wherein an equivalence of said extract of between 0.8 oz. and 2 oz. of said plant is included in every 10 oz. of said composition, based on dry weight.

9. A anti-microbial composition comprising:

an anti-microbially effective amount of an extract of a plant selected from the group consisting of: *Ranunculus, Ranunculus acer, Ranunculus acris, Ranunculus apiifolius, Ranunculus aquatilis, Ranunculus arvensis, Ranunculus asiaticus, Ranunculus bulbosus, Ranunculus bullatus, Caltha phylloptera, Clematis aristata, Ranunculus californicus, Ranunculus cantoniensis, Ranunculus cassius, Ranunculus collicola, Ranunculus collinus, Ranunculus communis, Ranunculus creticus, Ranunculus decurvus, Ranunculus falcatus, Ranunculus fascicularis, Ranunculus ficaria, Ranunculus flagelliformis, Ranunculus flammula, Ranunculus glaberrimus, Ranunculus glabrifolius, Ranunculus gunnianus, Ranunculus hiatus, Ranunculus japonicus, Ranunculus lanuginosus, Ranunculus lappaceus, Ranunculus lingua, Ranunculus multifidus, Ranunculus muricatus, Ranunculus nanus, Ranunculus occidentalis, Ranunculus parnassifolius, Ranunculus parviflorus, Ranunculus pascuinus, Ranunculus pennsylvanicus, Ranunculus petiolaris, Ranunculus pimpinellifolius, Ranunculus pinnatus, Ranunculus pubescens, Ranunculus pumilio, Ranunculus pusillus, Ranunculus repens, Ranunculus rivularis, Ranunculus scapiger, Ranunculus sceleratus, Ranunculus sp, Ranunculus stoloniferus, Ranunculus sylvestris, Ranunculus trichophyllus, Ranunculus triplodontus, Ranunculus zuccarinii, Anemone pulsatilla* and *Anemone pratensis*;

an essential oil; and a surfactant.

10. A anti-microbial composition as claimed in claim 9, wherein said plant *Ranunculus acris*.

11. A anti-microbial composition as claimed in claim 9, wherein said essential oil is tea tree oil.

12. A anti-microbial composition as claimed in claim 11, wherein between 0.1 oz. to 0.5 oz. of said tree oil is included in every 10 oz. of said composition, based on dry weight.

13. A anti-microbial composition as claimed in claim 9, wherein said surfactant is soap.

14. A anti-microbial composition as claimed in claim 9, wherein an equivalence of said extract of between 0.2 oz. and 5 oz. of said plant is included in every 10 oz. of said composition, based on dry weight.

15. A anti-microbial composition as claimed in claim 9, wherein an equivalence of said extract of between 0.8 oz. and 2 oz. of said plant is included in every 10 oz. of said composition based on dry weight.

16. A method of disinfecting an object comprising the step of:

contacting the object with a composition comprising an anti-microbially effective amount of an extract of a plant selected from the group consisting of: *Ranunculus, Ranunculus acer, Ranunculus acris, Ranunculus apiifolius, Ranunculus aquatilis, Ranunculus arvensis, Ranunculus asiaticus, Ranunculus bulbosus, Ranunculus bullatus, Caltha phylloptera, Clematis aristata, Ranunculus californicus, Ranunculus cantoniensis, Ranunculus cassius, Ranunculus collicola, Ranunculus collinus, Ranunculus communis, Ranunculus creticus, Ranunculus decurvus, Ranunculus falcatus, Ranunculus fascicularis, Ranunculus ficaria, Ranunculus ficaria, Ranunculus flagelliformis, Ranunculus flammula, Ranunculus glaberrimus, Ranunculus glabrifolius, Ranunculus gunnianus, Ranunculus hiatus, Ranunculus japonicus, Ranunculus lanuginosus, Ranunculus lappaceus, Ranunculus lingua, Ranunculus multifidus, Ranunculus muricatus, Ranunculus nanus, Ranunculus occidentalis, Ranunculus parnassifolius, Ranunculus parviflorus, Ranunculus pascuinus, Ranunculus pennsylvanicus, Ranunculus petiolaris, Ranunculus pimpinellifolius, Ranunculus pinnatus, Ranunculus pubescens, Ranunculus pumilio, Ranunculus pusillus, Ranunculus repens, Ranunculus rivularis, Ranunculus scapiger, Ranunculus sceleratus, Ranunculus sp, Ranunculus stoloniferus, Ranunculus sylvestris, Ranunculus trichophyllus, Ranunculus triplodontus, Ranunculus zuccarinii, Anemone pulsatilla* and *Anemone pratensis*.

17. A method as claimed in claim 16, wherein the step of contacting comprises the step of wiping a surface of the object with a towelette comprising said composition.

18. A method as claimed in claim 16, wherein the step of contacting comprises the step of rinsing a surface of the object using a solution comprising said composition.

19. A method as claimed in claim 16, wherein the step of contacting comprises the step of spraying a surface of the object using a solution comprising said composition.

20. A method as claimed in claim 16, wherein said plant is *Ranunculus acris*.

21. A method as claimed in claim 16, wherein said composition further comprises an essential oil having antiseptic properties.

22. A method as claimed in claim 21, wherein said essential oil is tea tree oil.

23. A packaged towelette comprising:

a sheet; and a surfactant, and an anti-microbially effective amount of an extract of a plant selected from the group consisting of: *Ranunculus, Ranunculus acer, Ranunculus acris, Ranunculus apiifolius, Ranunculus aquatilis, Ranunculus arvensis, Ranunculus asiaticus, Ranunculus bulbosus, Ranunculus bullatus, Caltha phylloptera, Clematis aristata Ranunculus californicus, Ranunculus cantoniensis, Ranunculus cassius, Ranunculus collicola, Ranunculus collinus, Ranunculus communis, Ranunculus creticus, Ranunculus decurvus, Ranunculus falcatus, Ranunculus fascicularis, Ranunculus ficaria, Ranunculus flagelliformis, Ranunculus flammula, Ranunculus, glaberrimus, Ranunculus glabrifolius, Ranunculus gunnianus, Ranunculus hiatus, Ranunculus japonicus, Ranunculus lanuginosus, Ranunculus lappaceus, Ranunculus lingua, Ranunculus multifidus, Ranunculus muricatus, Ranunculus nanus, Ranunculus occidentalis, Ranunculus parnassifolius, Ranunculus parviflorus, Ranunculus pascuinus, Ranunculus pennsylvanicus, Ranunculus petiolaris, Ranunculus pimpinellifolius, Ranunculus pinnatus, Ranunculus pubescens, Ranunculus pumilio, Ranunculus pusillus, Ranunculus repens, Ranunculus rivularis, Ranunculus scapiger, Ranunculus sceleratus, Ranunculus sp, Ranunculus stoloniferus, Ranunculus sylvestris, Ranunculus trichophyllus, Ranunculus triplodontus, Ranunculus zuccarinii, Anemone pulsatilla* and *Anemone pratensis*.

* * * * *